United States Patent [19]
Ireland et al.

[11] Patent Number: 5,990,085
[45] Date of Patent: Nov. 23, 1999

[54] INHIBIN-HBC FUSION PROTEIN

[75] Inventors: James J. Ireland, East Lansing, Mich.; Paul Pumpens, Riga, Latvia; Galina Borisova, Riga, Latvia; Dace Skrastina, Riga, Latvia; Guna Mezule, Riga, Latvia

[73] Assignee: Michigan State University, East Lansing, Mich.

[21] Appl. No.: 09/072,323

[22] Filed: May 4, 1998

[51] Int. Cl.[6] .......................... C07K 14/00; C07K 14/02; C07K 14/575; A61K 38/16
[52] U.S. Cl. .................................. 514/12; 514/2; 530/399; 536/23.4; 435/69.7
[58] Field of Search .......................... 514/12, 2; 530/350, 530/399; 536/23.4, 23.51; 435/69.7

[56] References Cited

PUBLICATIONS

Borisova, et al. *Proc. USSR Acad. Sci.,* 1988; 298:1474–1478 (no title).
Borisova, et al. *FEBS Lett.,* "Recombinant core particles of hepatitis B virus exposing foreign antigenic determinants on therir surface", 1989; 259:121–124.
Borisova, et al. *Intervirology,* "Spatial structure and insertion capacity of immunodominant region of hepatitis B core antigen", 1996; 39:16–22.
Brown, et al. *J. Reprod. Fertility,* "Immunization against recombinant bovine inhibin α–subunit causes increased ovulation rates in gilts", 1990; 90:199–205.
Devereux, et al. *Nucleic Acids Res.,* "A comprehensive set of sequence analysis programs for the VAX", 1984; 12:387–395.
Furst, et al. *Gene,* 1986; 48:119–131 (no title).
Good, et al. *Biol. Reprod.,* "Isolation of nine different biologically and immunologically active molecular variants of bovine follicular inhibin", 1995; 53:1478–1488.
Ireland, et al. *Biol. Reprod.,* "Alterations in amounts of different forms of inhibin during follicular atresia", 1994; 50:1265–1276.
King, et al. *J. Animal Science,* "Ovulatory and endocrine responses after active immunization of gilts against a synthetic fragment of bovine inhibin", 1993; 71:975–982.
Martin, et al. *Biol. Reprod.,* "Immunoneutralization of inhibin modifies hormone secretion and sperm production in bulls", 1991; 45:73–77.
Mason, et al. *TIBTECH,* "Transgenic plants as vaccine production systems", 1995; 13:388–392.
McCue, et al. *Theriogenology,* "Ovulation and embryo recovery rates following immunization of mares against an inhibin alpha–subunit fragment", 1992; 38:823–831.
Morris, et al. *J. Reprod. Fertility,* "Effect of immunization against synthetic peptide sequences of bovine inhibin α–subunit on ovulation rate and twin–calving rate in heifers", 1993; 97:255–261.
Nassal, et al. *Trends in Microbiology,* "Hepatitis B virus replication", 1993; 1:221–228.
Ohsawa, et al. *Anal. Biochem.,* "Silver stain for detecting 10–femtogram quantities of protein after polyacrylamide gel electrophoresis", 1983; 135:409–415.
Ouchterlony 1965, In:*Immunochemie. 15th Colloquium of the Gesellschaft fur Physiologische,* Chemie, Springer, Berlin, Heidelberg, New York, 1979; pp. 15–35.
Scott, et al. *Science,* "Searching for peptide ligands with an epitope library", 1990; 249:386–390.
Towbin, et al. *PNAS USA,* "Electrophoretic transfer of proteins from polyacrylamide gels to nitrocellulose sheets: Procedure and some applications", 1979; 76:4350–4354.
Voglmayr, et al. *Biol. Reprod.,* "Immunization of rams against human recombinant inhibin α–subunit delays, augments, and extends season–related increase in blood gonadotropin levels", 1990; 42:81–86.

*Primary Examiner*—Elizabeth Kemmerer
*Attorney, Agent, or Firm*—Merchant & Gould

[57] ABSTRACT

A fusion protein formed of an antigenic inhibin peptide inserted into hepatitis B capsid protein is expressed from a chimeric gene forming an effective immunogen which induces anti-inhibin antibodies when administered to a host animal.

19 Claims, 6 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 75 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:1:

```
TCTACCCCGC CGCTGCCGTG GCCGTGGTCC CCGGCTGCTC TGCTGCAGCG TCCGCCGGAA      60

GAACCGGCTG CTCCG                                                      75
```

(2) INFORMATION FOR SEQ ID NO:2:

(i) SEQUENCE CHARACTERISTICS:
      (A) LENGTH: 75 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:2:

```
AGATCCGGCG GCGACGGCAC CGGCACCAGG GGCCGACGAG ACGACGTCGC AGGCGGCCTT      60

CTTGGCCGAC GAGGC                                                      75
```

(2) INFORMATION FOR SEQ ID NO:3:

(i) SEQUENCE CHARACTERISTICS:
      (A) LENGTH: 89 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

```
GGGCCCTCTA CCCCGCCGCT GCCGTGGCCG TGGTCCGYCC GGCTGCTCTG CTGCAGCGTC      60

CGCCGGAAGA ACCGGCTGCT CCGGGGTAA                                       89
```

(2) INFORMATION FOR SEQ ID NO:4:

(i) SEQUENCE CHARACTERISTICS:
      (A) LENGTH: 27 amino acids
      (B) TYPE: amino acid
      (C) STRANDEDNESS: unknown
      (D) TOPOLOGY: linear (ii) MOLECULE TYPE: peptide (xi) SEQUENCE DESCRIPTION: SEQ ID NO:4:

```
Gly Pro Ser Thr Pro Pro Leu Pro Trp Trp Ser Pro Ala Ala Leu Leu
 1               5                  10                  15

Gln Arg Pro Pro Glu Glu Pro Ala Ala Pro Gly
             20                  25
```

(2) INFORMATION FOR SEQ ID NO:5:

```
       (i) SEQUENCE CHARACTERISTICS:
           (A) LENGTH: 87 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:5:

GATCACTCTA CCCCGCCGCT GCCGTGGCCG TGGTCCCCGG CTGCTCTGCT GCAGCGTCCG      60

CCGGAAGAAC CGGCTGCTCC GGTAGAT                                         87

(2) INFORMATION FOR SEQ ID NO:6:

(i) SEQUENCE CHARACTERISTICS:
           (A) LENGTH: 28 amino acids
           (B) TYPE: amino acid
           (C) STRANDEDNESS: unknown
           (D) TOPOLOGY: linear (ii) MOLECULE TYPE: peptide (xi) SEQUENCE DESCRIPTION: SEQ ID NO:6:

Asp His Ser Thr Pro Pro Leu Pro Trp Trp Ser Pro Ala Ala Leu Leu
1               5                  10                  15

Gln Arg Pro Pro Glu Glu Pro Ala Ala Pro Val Asp
            20                  25
```

INHIBIN-HBC FUSION PROTEIN

FIELD OF THE INVENTION

This invention relates to useful immunogenic molecules formed of an antigenic inhibin peptide and hepatitis B capsid protein. More particularly, an antigenic inhibin peptide is genetically inserted into the hepatitis B capsid protein, resulting in the production of a fusion protein which induces the production of anti-inhibin antibodies when administered to host animals, even in the absence of adjuvant.

BACKGROUND OF THE INVENTION

The inhibin protein family includes dimeric glycoproteins produced by the gonads which act in an endocrine fashion to suppress secretion of follicle stimulating hormone (FSH) from the pituitary gland. Since FSH is the major hormone involved in stimulation of ovulation and sperm production, inhibin-induced suppression of FSH diminishes the rates of ovulation and sperm production. Inhibins are therefore natural suppressers of the reproductive process.

Active immunization of farm animals against inhibin increases the rates of ovulation and sperm production, demonstrating that inhibin-based immunogens are important agents to enhance fertility in farm animals, including swine, bovine, ovine, and equine animals. See, for example: Brown, et al., *J.Reprod.Fertility* 90:199–205, 1990; King, et al., *J.Animal Science* 71:975–982, 1993; Morris, et al., *J.Reprod.Fertility* 97:255–261, 1993; McCue, et al., *Theriogenology* 38:823–831, 1992; Voglmayer, et al., *Biol.Reprod.* 42:81–86, 1990; Martin, et al., *Biol.Reprod.* 45:73–77, 1991.

The immunization of gilts with a small peptide fragment of the bovine inhibin $\alpha_c^{1-26}$ subunit chemically conjugated to human alpha globulin (HAG) and mixed with Freund's adjuvant resulted in a minor increase in FSH during the follicular phase and a decrease in FSH during the luteal phase, without effect on serum concentrations of estradiol, progesterone, or luteinizing hormone (King, et al., *J. Animal Science* 71:975–982, 1993). Despite the relatively minor increase in FSH during the follicular phase and decrease during the early luteal phase, immunized gilts had a 39% greater ovulation rate as compared with controls. In addition, lifetime proliferacy of the immunized gilts was enhanced.

While the above described merits of using the antigenic inhibin peptide to neutralize inhibins and enhance fertility are known, a commercially useful vaccine is not available.

The development of vaccines based on small antigenic epitopes is hampered by the inability of the small antigen to elicit a good immune response in a host animal. The use of carrier immunogens provides some assistance in the immune response, but often decreases the specific activity and yield of the response against the desired antigen. Methods for conjugation of antigens to carrier agents are costly, and generally utilize hazardous chemicals. Covalent coupling of antigen to a carrier protein is inherently variable, resulting in an antigen with an imprecise structure, compromising vaccine potency. The use of adjuvants also tends to decrease the yield of specific antibodies and can be harmful to the animal host, causing abscesses, skin lesions, and hypersensitivity. These factors are unacceptable for the production of a commercially useful vaccine.

These disadvantages are overcome in the present invention by using recombinantly produced fusion proteins as immunogens, whose structure is well defined. Synthesis of the inventive immunogens does not require hazardous chemical treatments, and the molecules are herein demonstrated to induce a desired anti-inhibin immune response, even in the absence of additional adjuvants.

SUMMARY OF THE INVENTION

It has now been found that an inhibin:hepatitis B capsid protein fusion (Inh:HBc) provides a useful, defined, easily produced, immunogenic molecule which, upon administration to host animals, induces a fertility-enhancing, anti-inhibin immune response, even in the absence of additional adjuvant. The Inh:HBc fusion protein is produced by inserting a first nucleic acid sequence encoding an antigenic inhibin peptide into a second nucleic acid sequence encoding hepatitis B capsid protein and expressing a fusion protein a cellular host. When administered to host animals, particularly to farm animals, the Inh:HBc fusion protein induces an anti-inhibin immune response The anti-inhibin response results in enhanced fertility, measured, for example, as an increase in ovulation rates in immunized animals, and preferably, as an increase in lifetime proliferation.

In a preferred embodiment of the invention, a preferred antigenic inhibin peptide is an amino acid sequence of the inhibin $\alpha_c$ subunit. For example, a preferred antigenic peptide of the invention is formed of the first 25 N-terminal amino acids of the inhibin alpha-C subunit (bINH$\alpha_c^{1-25}$).

It was unexpectedly discovered that inhibin antigenic peptide inserted at position 78 of the HBc protein results in a preferred fusion protein inducing useful antibody titer in host animals with good anti-inhibin specificity. In this construct, the inhibin antigenic peptide is inserted in place of a major immunological region of HBc Ag.

DETAILED DESCRIPTION OF THE INVENTION

Figure 1A:
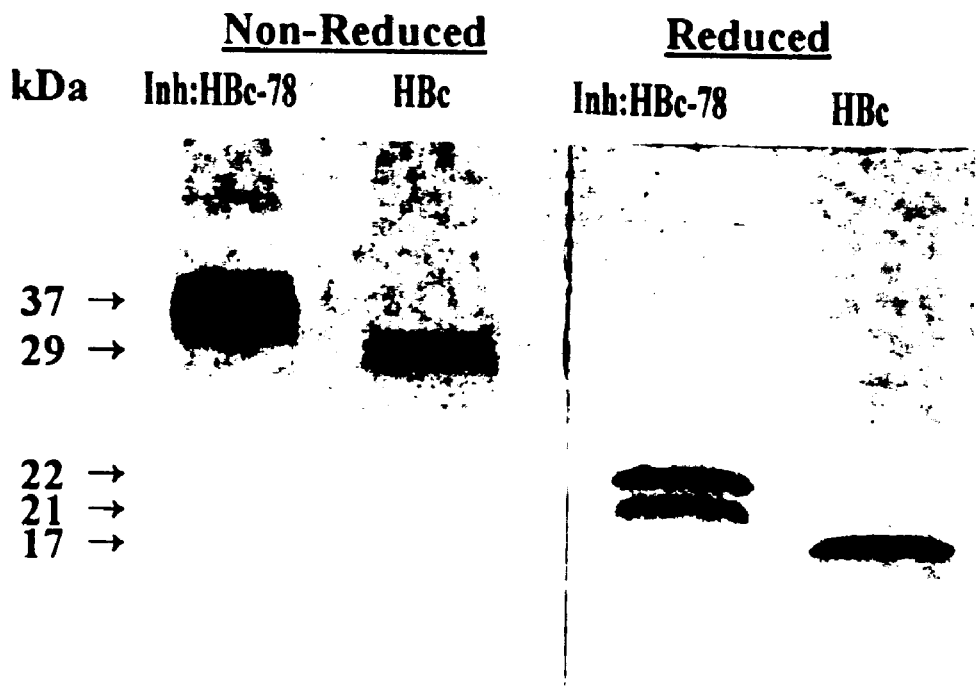
FIG. 1A is a photograph of a silver stained gel showing production of Inh:HBc-78.
Figure 1B:
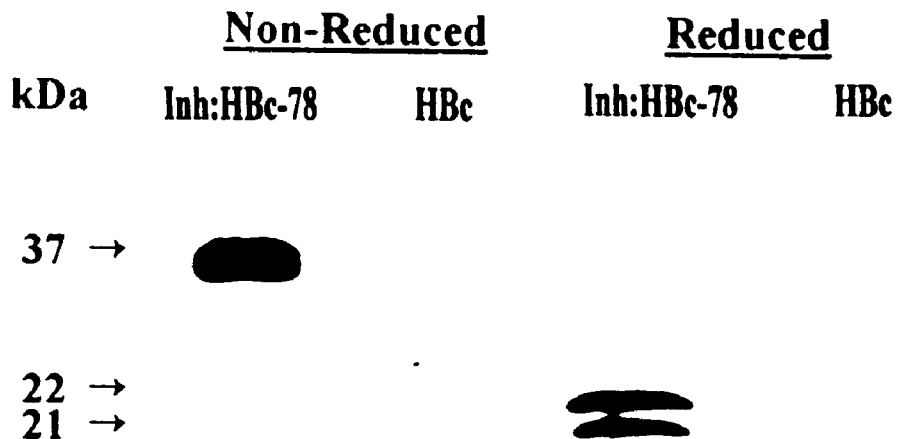
FIG. 1B is a photograph of an immunoblot of Inh:HBc-78 probed with anti-inhibin antibody.
Figure 1C:
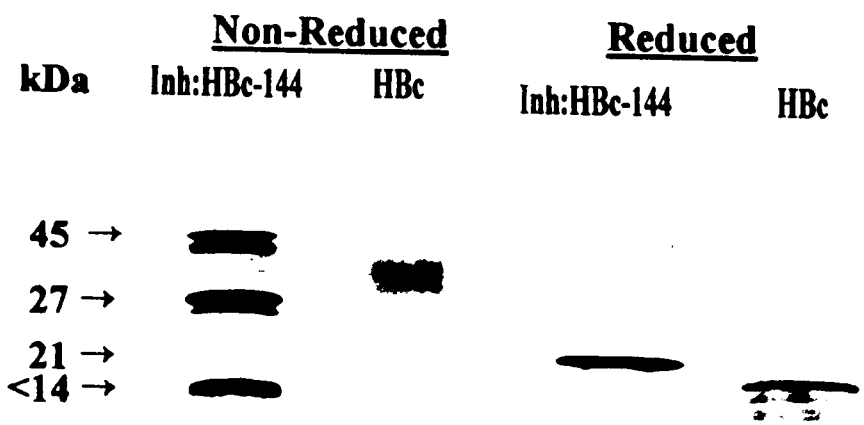
FIG. 1C is a photograph of a silver stained gel showing production of Inh:HBc-144.
Figure 1D:
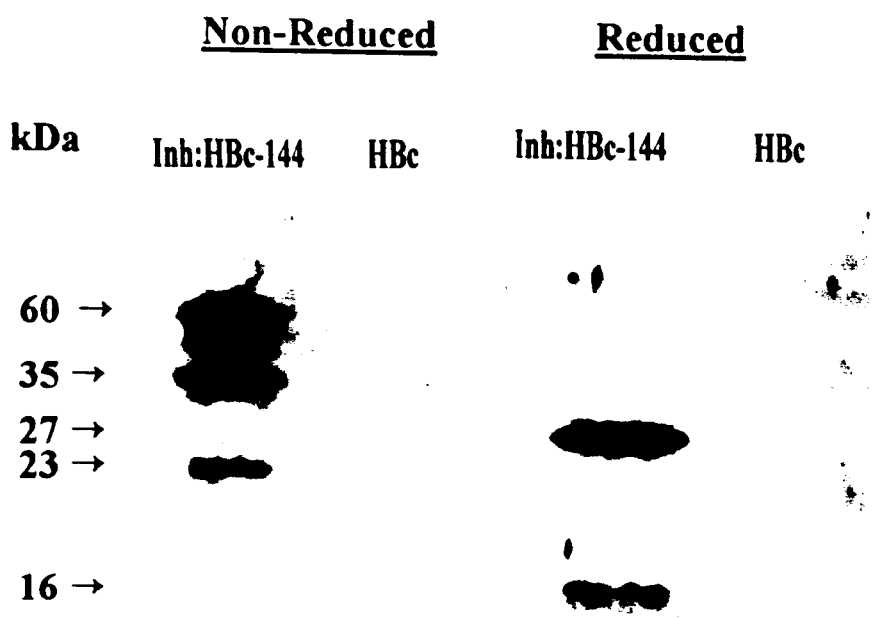
FIG. 1D is a photograph of an immunoblot of Inh:HBc-144 probed with anti-inhibin antibody.

In the preferred embodiments of the invention, an immunogenic carrier molecule, the hepatitis B capsid protein (HBc), is modified to include an inserted antigenic inhibin peptide. The inserted inhibin peptide is positioned such that it does not preclude correct assembly of the HBc protein into core particles and is recognized as antigenic in host systems. As shown below, the inhibin antigenic peptide is preferentially inserted at position 78 of the HBc protein.

When used as a vaccine, the Ihn:HBc fusion protein is effective in eliciting an antibody response against the antigenic peptide in host animals, particularly in farm animals. Vaccination of a host animal with the Inh:HBc fusion protein results in the development of specific anti-inhibin antibodies in the animal, in the presence or absence of added adjuvant. Vaccination and induction of anti-inhibin antibodies results in enhanced fertility.

Antigenic Inhibin Peptides

Antigenic inhibin peptides useful in the present invention are generally short amino acid sequences, e.g., less than about 100 amino acids, preferably about 8–30 amino acids, and more preferably 10–25 amino acids in length. The peptide is preferably known to represent an epitope that is able to induce an immune response against inhibin, such as the first portion of the inhibin $\alpha_c$ chain, amino acids 1–30. For example, the antigenic peptide may be known to produce a desired antigenic response when used in another carrier protein such as HAG or when used with an adjuvant system such as co-administration with Fruend's Adjuvant or other immunogen. Alternatively, the peptide antigen may be a portion of a known inhibin protein having a particularly unique amino acid sequence distinguishing it from other inhibin proteins. These and other techniques for identifying and screening potential antigenic peptides useful in vaccine development are generally known. See, for example, Scott, et al., 1990, *Science* 249:386–390.

Preferred inhibin antigenic peptides include portions of the $\alpha_c$ chain, e.g., 10–25 amino acids selected from known antigenic portions of the molecule. Most preferred is a sequence of 10–25 amino acids of the first 30 amino acids of the $\alpha_c$ chain.

Antigenic peptides are inserted into the HBc molecule by recombinant DNA methods. For example, a synthetic nucleic acid sequence or vector containing a nucleic acid sequence encoding a desired inhibin antigenic peptide to be inserted into HBc is specifically designed to include restriction endonuclease sites matched to a specified endonuclease-cut nucleic acid sequence encoding HBc. Where a desirable HBc insertion site contains a single, unique restriction endonuclease site, the inhibin antigen's nucleic acid sequence is preferably engineered to include matched restriction sites at both ends of the sequence. In this manner, the sequence encoding the inhibin antigen is inserted into the HBc sequence without removal of any HBc-encoding nucleotides. Care is taken to match the antigenic inhibin-encoding nucleic acid sequence to be inserted with the reading frame of the HBc sequence so that normal expression of the encoded HBc with the encoded inhibin antigen is achieved.

For HBc, specific display vectors containing cloning sites specifically engineered into the HBc nucleic acid sequence have been constructed. In these vectors, expression of the HBc gene is under the control of a tandem stretch of strong *E. coli* trp promoters. Vector pCT31, prepared as described in Borisova, et al., 1988, *Proc. USSR Acad. Sci.* 298:1474–1478 and Borisova, et al., 1989, *FEBS Lett.* 259:121–124 (containing a truncated form of HBc with amino acids 145–183 removed), is designed for insertion of antigens at amino acid position 144, and allows in-frame insertion and translation termination in all three possible frames. Vector p2-19, prepared as described in Borisova, et al., 1996, *Intervirology* 39:16–22, is designed for insertion of antigens at amino acid position 78, and allows for blunt-ended insertion of the antigenic fragment in frame.

It is contemplated that the compositions and methods of the invention may be limited by the antigenic peptide's amino acid chain length (e.g., less than 100 amino acids, and preferably no greater than about 30 amino acids), net charge of the inserted amino acid sequence (e.g., less than about 50% highly charged amino acid residues), potentially cross-linking residues, or a density of potentially self-hybridizing nucleic acid sequences. These limitations are generally known and can be recognized by review of the amino acid sequence to be inserted.

It is generally known that a nucleic acid sequence may be modified for enhanced expression in a particular host cell by modifying the codons of the nucleic acid sequence to those more preferred in the specific host cell. Thus, for example, to express the Inh:HBc fusion protein in *E. coli*, the peptide sequence is back translated into the nucleotide sequence using the codon frequency found in *E. coli* proteins, as determined, for example, by the GCG computer program (Devereaux, et al., 1984, *Nucleic Acids Res.* 12:387–3905) and modified as suggested by *E. coli* codon frequencies.

It is generally understood that protein expression in a given host cell may be enhanced by modification of one or more nucleotides in the coding sequence to reduce the number of unique or rare codons. In a preferred embodiment of the invention, the nucleic acid sequence contains one or more codons modified according to the codon frequency preferences for a particular cellular host.

Inhibin Vaccine

Inhibin is a glycoprotein produced by the gonads that selectively suppresses the secretion of follicle stimulating hormone (FSH) from the anterior pituitary gland. Vaccination against inhibin decreases available inhibin, with a resulting increase in levels of follicle stimulating hormone (FSH), and enhanced fertility. Enhanced fertility may be due to enhanced production of sperm or ova, to increased rates of ovulation or spermatogenesis, or to increased lifetime proliferacy in animals, for example.

Immunization of animals with bovine inhibin—$\alpha_c$ subunit has demonstrated the usefulness of inhibin-based antigens as fertility-enhancing vaccines. However, to date, a practical commercial vaccine has not been produced, at least in part due to the limitations of chemical synthesis, conjugation, and adjuvant toxicity discussed above.

In a preferred embodiment and exemplary of the invention, the nucleic acid sequence encoding the first 25 N-terminal residues of the antigenic inhibin $\alpha_c$ subunit ($\alpha_c^{1-25}$) is inserted into nucleic acid sequence encoding HBc such that the expressed fusion protein will include the inhibin antigenic peptide inserted at HBc amino acid position 78 (Inh:HBc-78). Multiple copies of the antigen may be inserted, e.g., at more than one site in the HBc molecule, and preferably at two or more sites, where at least one inhibin antigen insertion site is at position 78.

The chimeric gene encoding the Inh:HBc fusion protein is subcloned into an expression vector, preferably a broad-host-range expression vector. The inserted antigen is expressed with expression of the HBc molecule, such that when the expressed fusion protein is administered to host animals, an anti-inhibin immune response is produced in the animals, reducing endogenous inhibin and thereby enhancing fertility in treated animals.

Hepatitis B Capsid Protein

The hepatitis B capsid protein (HBc) is an immunogenic carrier protein having several advantages over other potential carrier molecules (Nassal, et al., *Trends in Microbiology* 1:221–228, 1993). These advantages include high level production and correct assembly into core particles in the absence of virus in a wide variety of eukaryotic and prokaryotic expression systems. Because recombinant HBc molecules expressed in *E. coli* self-assemble into particles containing 180 or 240 subunits, an inserted inhibin antigen is present in 180 or 240 copies per particle.

A hepatitis B capsid fusion protein including an antigenic inhibin peptide, capable of inducing the production of anti-inhibin antibodies in a host animal, preferably in the absence of adjuvant, would be very useful, particularly for enhancing the fertility of farm animals.

Cellular Hosts

Many known cellular host systems are suitable for expression of the chimeric genes of the invention. For example, non-pathogenic strains such as Vibrio and including *Vibrio anguillarium* are transfected with suitable vectors containing the gene encoding Inh:HBc and express the fusion protein. Suitable vectors for use in Vibrio include pJF118, as described in Furst, et al, 1986, *Gene* 48:119–131.

Additional host systems useful in the invention include *E. coli,* useful for example with the HBc display vectors described more fully in the examples below, as well as other known host and vector systems.

HBc is a known immunogen. The fusion protein immunogen of the invention, formed of the intact HBc protein and an inserted antigenic inhibin peptide, is administered to farm animals such as sheep, pigs, horses, cows, and the like, according to the methods known as effective for the immunogenic administration of HBc and other protein immunogens.

Administration methods include injection, e.g., intramuscular, subcutaneous, or intraperitoneal injection and nasal administration of protein compositions to induce effective antibody titers. In a preferred embodiment, the fusion protein of the invention is expressed in edible plants or animals for oral ingestion. This oral delivery method has been described for immunogenic delivery of the immunogen LTB. See, for example, Mason, et a l., 1995, *TIBTECH* 13:388–392, describing oral immunization against LTB via ingestion of transgenic potato tubers expressing LTB antigen.

EXAMPLES

The present invention may be better understood with reference to the following examples. These examples are intended to be representative of specific embodiments of the invention, and are not intended as limiting the scope of the invention.

Example 1

Production of In:HBc Fusion Protein

HBc Display Vectors

Hepatitis B capsid antigen display vectors containing the HBc gene under the control of a tandem string of strong *E. coli* trp promoters (Borisova, et al. 1988, *Proc. USSR Acad.Sci.* 298:1474–1478; Borisova, et al., *FEBS Lett.* 259:121–124, 1989; and Borisova, et al., 1996, *Intervirology* 39:16–22) were used to insert the bovine inhibin $\alpha_c^{1-25}$ (bINH-$\alpha_c^{1-25}$) antigenic epitope into HBc at amino acid positions 144 and 78. Vector pCT31 was used for insertions into position 144, and allowed in-frame insertion and translation termination in all three possible frames to produce Inh:HBc-144. Vector p2-19 was used for insertions into position 78, allowing for blunt-ended insertion of the antigenic fragment in frame to produce Inh:HBc-78.

Inhibin Antigenic Peptide

The Inhibin antigenic peptide was prepared by synthesizing the following oligonucleotides:

```
                                          [SEQ.ID.NO:1]
5'-TCT ACC CCG CCG CTG CCG TGG CCG TGG TCC CCG
GCT GCT CTG CTG CAG CGT CCG CCG GAA GAA CCG
GCT GCT CCG-3'; and
                                          [SEQ.ID.NO:2]
3'-CGG AGC AGC CGG TTC TTC CGG CGG ACG CTG CAG
CAG AGC AGC CGG GGA CCA CGG CCA CGG CAG CGG
CGG CCT AGA-5'.
```

Each oligonucleotide was phosphorylated by T4 polynucleotide kinase, and the pair of oligonucleotides was annealed to form a double-strand. The double-stranded nucleic acid sequence was then cloned as a blunt-ended fragment into the HBc display vectors to form chimeric genes encoding the Inh:HBc fusion proteins.

Cloning

Ampicillin-resistant plasmid pCT31 carrying the C-terminally truncated (having amino acids 145–183 removed) HBc gene was used as a vector. For insertion at amino acid 144, the vector was cleaved with SmaI (IMB Fermentas, Vilnius, Lithuania) at position 1741, purified from agarose gel by the DEAE paper method, and used for ligation with the inhibin antigenic double-stranded nucleic acid sequence described above as phosphorylated or dephosphorylated by bacterial alkaline phosphatase (IMB Fermentas). Ligation was performed in 20 mM TRIS pH 7.6, 0.5 mM $MgCl_2$, 5 mM dithiothreitol (in 10 μl) with 100 ng vector and fragment, 1 Weiss unit of T4 DNA ligase, at 4° C. for 12 hours. The molar ratio of oligonucleotide:vector was either 5:1 or 100:1.

For insertion at amino acid 78, ampicillin-resistant plasmid p2-19 carrying the HBc gene with a polylinker inserted at position 78 was also used as a vector. Polylinker encodes an immunomarker sequence "DPAFR" recognized by monoclonal anti-preS1 antibody MA18/7 (W. H. Gerlich, Giessen). The p2-19 vector was cleaved simultaneously by Eco 721 (position 1531) and Eco 1051 (position 1552) (IBM Fermentas), purified from agarose gel by DEAE paper method, dephosphorylated by bacterial alkaline phosphatase, and used for ligation with the double-stranded antigenic inhibin peptide. The oligonucleotide:vector molar ratio was 100:1.

First selection of plasmids containing the antigenic inhibin insert was by Pst1 cleavage. The vector contains a unique Pst1 cleavage site at position 4742. Clones containing the Pst1 site in the insert (presenting two fragments) were subjected to further screening by immunoblotting and sequencing.

Purified Fusion Protein

*E. coli* strain RR1 (F-, hsd S20 ($r_b$-, $m_b$-), recA+, ara-14, proA2, lacY1, galK2, rpsL20 ($Sm^1$), xyl-5, mlt-1, supE44, λ–) was used for transformation with the chimeric Inh:HBc vectors, resulting in a transformation efficiency of $10^9$ clones/μg of supercoiled DNA. Recombinant fusion protein was purified from cells by cell lysis followed by Sepharose CL4B column chromatography. Production yield for the fusion protein Inh:HBc-144 was higher than for Inh:HBc-78, generating 5 mg of purified intact product per liter of *E. coli* cells.

Immunoblot Screening

Transformed *E. coli* cells expressing the fusion protein were selected by immunoblotting and sequencing. For selection by immunoblotting, *E. coli* strain K802 cells harboring the appropriate plasmids were grown to saturation overnight in M9 synthetic medium supplemented with 2% g/l Casamino acids (Difco). Bacteria were pelleted, suspended in SDS-gel electrophoresis sample buffer containing 2% SDS and 2% 2-mercaptoethanol, and lysed by heating at 100° C. for five minutes. Proteins were separated by PAGE in a slab gel (150×150×0.75 mm) apparatus.

Western blotting was conducted as described by Towbin et al., *PNAS* USA,76:4350–4354, 1979. Aliquots (4 μg) of the fusion proteins In3-69 and In4-56, as well as control vector HBc were subjected to 15% SDS-PAGE under non-reducing conditions. Each gel was stained for protein by the silver stain method described, for example, in Ohsawa, et al., *Anal. Biochem.*135:409–415, 1983.

Parallel gels containing 100 ng aliquots of the fusion protein and control HBc were run under both non-reducing and reducing conditions. Separated protein was electrophoretically transferred to Immobilon P membrane (Millipore), and processed for immunoblot assay with mink anti-bovine $\alpha_c^{1-26}$ gly.tyr antiserum as described in Good, et al., *Biol.Reprod.* 53:1478–1488, 1995. The protein-transferred membranes were incubated with the anti-inhibin antibody at a dilution of 1:1000 in TTBS overnight at room temperature, as described in Ireland, et al., *Biol.Reprod.* 50:1265–1276, 1994.

After washing in TTBS (five 10-minute washes), the membranes were further incubated in 20 ml of $^{125}$I-bINHα$_c^{1-26}$ gly.tyr (1×10$^6$ cpm/ml in TTBS with 1% gelatin) for competition. The membrane was washed and placed on X-ray film (Kodak X-OMAT AR) with a Cronex intensifying screen and exposed for ten days at −80° C.

As show in FIGS. 1A–D, the silver-stained gels as compared with the immunoblots demonstrated the purity of the fusion protein preparations. The immunoblots further demonstrated immunoreactivity of the fusion proteins with anti-inhibin antibody.

DNA Sequencing of Positive Clones

The primary structure of the DNA insert in the positive clones was determined by DNA sequencing, using standard methods for Sanger's dideoxy sequencing. Two different clones were selected for sequence analysis, the first having the inhibin epitope inserted at amino acid position 144 (Inh:HBc-144) and the second inserted at amino acid position 78 (Inh:HBc-78). The following sequences were identified, confirming the insertion of the antigenic inhibin peptide sequence shown below surrounded by HBc-polylinker sequences (in bold):

In position 144, clone In3-38, encoding Inh:HBc-144:

```
GGG CCC TCT ACC CCG CCG CTG CCG TGG CCG TGG TCC
Gly Pro Ser Thr Pro Pro Leu Pro Trp pro Trp Ser CCG GCT GCT CTG CTG CAG CGT CCG CCG GAA GAA CCG
Pro Ala Ala Leu Leu Gln Arg Pro Pro Glu Glu Pro GCT GCT CCG GGG TAA  [SEQ.ID.NO:3]
Ala Ala Pro Gly       [SEQ.ID.NO:4]
```

In position 78, clone In4-56, encoding Inh:HBc-78:

```
GAT CAC TCT ACC CCG CCG CTG CCG TGG CCG TGG TCC
Asp His Ser Thr Pro Pro Leu Pro Trp pro Trp Ser CCG GCT GCT CTG CTG CAG CGT CCG CCG GAA GAA CCG
Pro Ala Ala Leu Leu Gln Arg Pro Pro Glu Glu Pro GCT GCT CCG GTA GAT  [SEQ.ID.NO:5]
Ala Ala Pro Val Asp  [SEQ.ID.NO:6]
```

Self-Assembly

The Inh:HBc fusion protein self-assembled and remained intact after insertion of the antigenic inhibin peptide into HBc, as shown by double radial immunodiffusion against capsid specific antibodies, using the method of Ouchterlony, 1965, In: *Immunochemie. 15th Colloquium of the Gesellschaftfur Physiologische* Chemie, Springer, Berlin, Heidelberg, New York, 1979, pages 15–35. Gel filtration on Separose CL4B, and electron microscopy of negatively stained Inh:HBc fusion protein capsid preparations were also used to confirm correct assembly.

Natural human and hyperimmune rabbit anti-HBc antibodies were used as the particulate HBc-specific polyclonal antibodies for double radial immunidiffusion test according to Ouchterlony, supra. Hyperimmune anti-HBc antibodies were generated by immunization of rabbits with purified recombinant HBc (Mezule, BMC, Riga).

Figure 2:
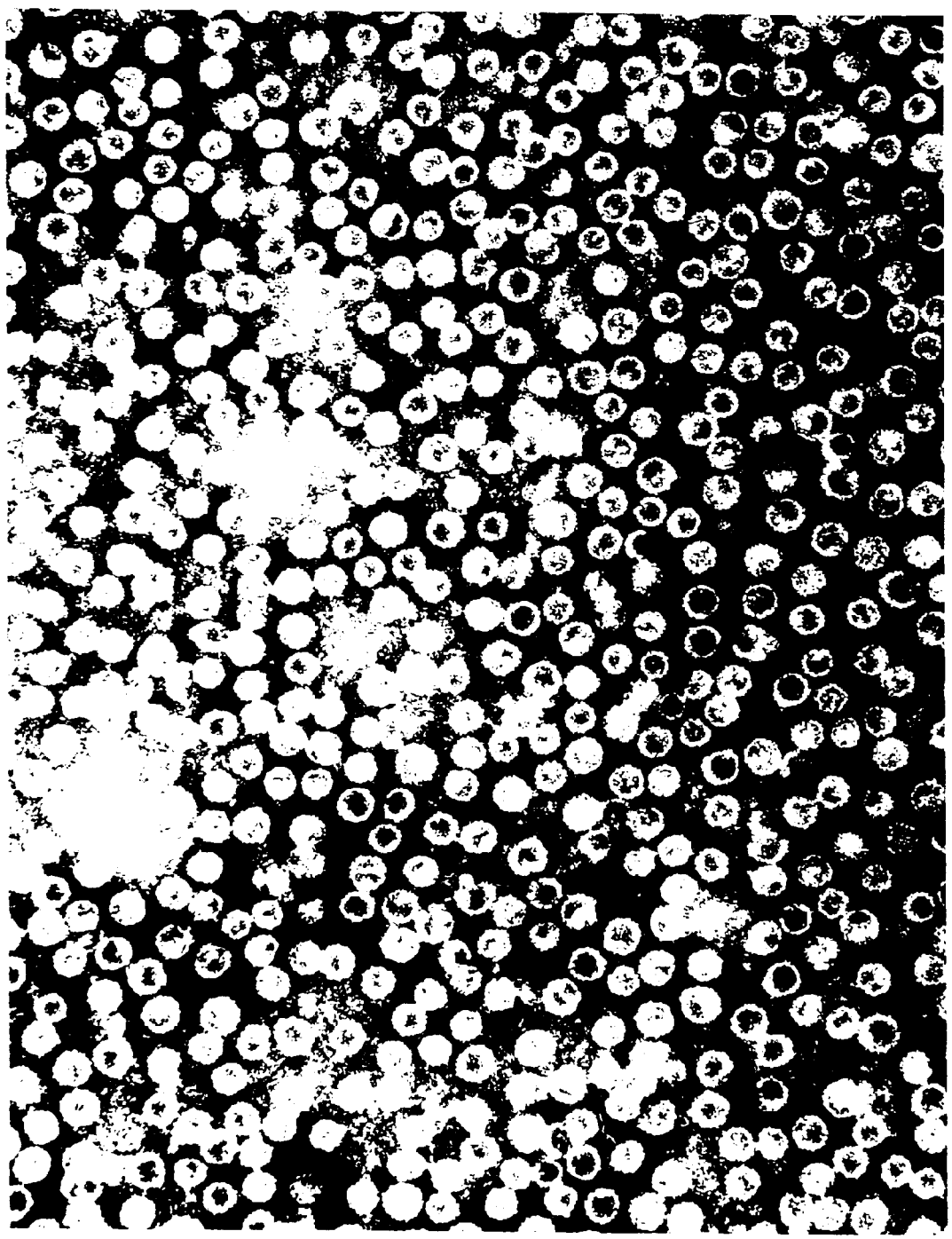
FIG. 2 is a electron micrograph showing capsid formation of Inh:HBc-78.

Ouchterlony's test for lysozyme lysates of the fusion proteins demonstrated their fill capability to self-assemble. Ouchterlony's assay employs the basic principles of double radial immunodiffusion in 0.8% agarose gel of antibodies (center) and antigens at the step 1:2 dilutions (radial) after 24 hours at 4° C. Titers of antibody are recognized as the last precipitation—line-forming dilution. These studies demonstrated the two fusion protein clones, Inh:HBc-144 (In3-38) and Inh:HBc-78 (In4-56) were able to form capsids (see FIG. 2).

Purification of Fusion Protein

Inh:HBc recombinants 144 (In3-38) and 78 (In4-56) were expressed in *E. coli* strain K802 harboring the appropriate plasmid encoding a recombinant gene under the control of a tandem string of strong bacterial trp promoters. Bacteria were grown overnight on a rotary shaker at 37° C. in 500 ml flasks containing 200 ml of M9 minimal medium supplemented with 1% Casamino acids (Difco) and 0.2% glucose. An optical density (650 nm) of 4–5 for one ml of the suspension was generally reached. Cells were pelleted and lysed with a 30 minute incubation on ice in lysis buffer containing 50 mM TRIS-HCl (ph 8.0), 5 mM EDTA, 100 μg/ml PMSF, 2 mg/ml lysozyme and then frozen and thawed three times. After freeze-thaw, 10 mM MgCl$_2$ and 20 μg/ml DNase were added. After low speed centrifugation, proteins were precipitated from the supernatant with ammonium sulphate at 30% saturation for 12 hours at 4° C. Pellets were resuspended in standard PBS buffer containing 0.1% Triton X-100 (30–40 mg/ml total protein). A volume of 5 ml of protein solution was loaded on a Sepharose CL4B column (2.5×85 cm) and eluted with PBS buffer without Triton X-100. Fractions containing caspids (detected by double radial immunodiffusion test against human polyclonal anti-HBc antibodies) were pooled and concentrated by ammonium sulphate precipitation at 50% saturation. Pellets were resuspended in TRIS-saline buffer (10 mM TRIS-HCl (pH 7.5), 150 mM NaCl) to a final concentration of about 10–15 mg/ml total protein, dialyzed overnight against 1000 volumes of the same buffer and stored at −70° C. Quality of capsid preparations was checked by electron microscopy (V. Ose, BMC, Riga). See FIG. 2.

Immunodiffusion, silver stained PAGE, and immunoblots with anti-HBc monoclonal 14E11 antibodies of SDS and lysozyme lysates of Inh:HBc-144 and Inh:HBc-78 cells were used to follow the purification process. On silver staining and immunoblot of gels run with the fusion protein, the inhibin fusion protein preparation was shown to be relatively pure. The immunoblot data demonstrated that only the fusion protein, and not the HBc vector reacted with anti-$\alpha_c^{1-25}$ antibodies. (See FIGS. 1A–D).

Example 2

Immunization of Mice with Inh:HBc Fusion Protein

A total of 45 BALB/C mice, 5 per treatment group, were immunized subcutaneously with 20 μg of the Inh:HBc fusion proteins 144 (In3-96) and 78 (In4-56), or with the HBc control, both in the presence and absence of Fruend's complete adjuvant (0.1 ml). One group of mice was untreated. The primary immunization was followed by four boosters spaced two weeks apart. Two weeks after boosts 1, 2, and 3, all mice were bled. A volume of 20 μl of blood was placed in PBS (1:10 dilution) containing heparin to prevent clotting. Each boost was given immediately following each bleed. Mice were sacrificed 2 weeks after boost 4, and trunk blood was collected.

The blood samples were analyzed for anti-inhibin antibody activity by ELISA. Microtiter plates (Xenobind, Xenopore, Inc.) were coated with 1 μg/well of bovine inhibin $\alpha_c^{1-26}$ peptide, and a solid phase, non-radiometric ELISA protocol was used to estimate titer. Absorbance at 490 nm ($A_{490}$) was measured using a microplate reader (BioRad Model 35500). Titer was defined as the serum/plasma dilution giving an A490 four times the average value for untreated controls.

Figure 3:
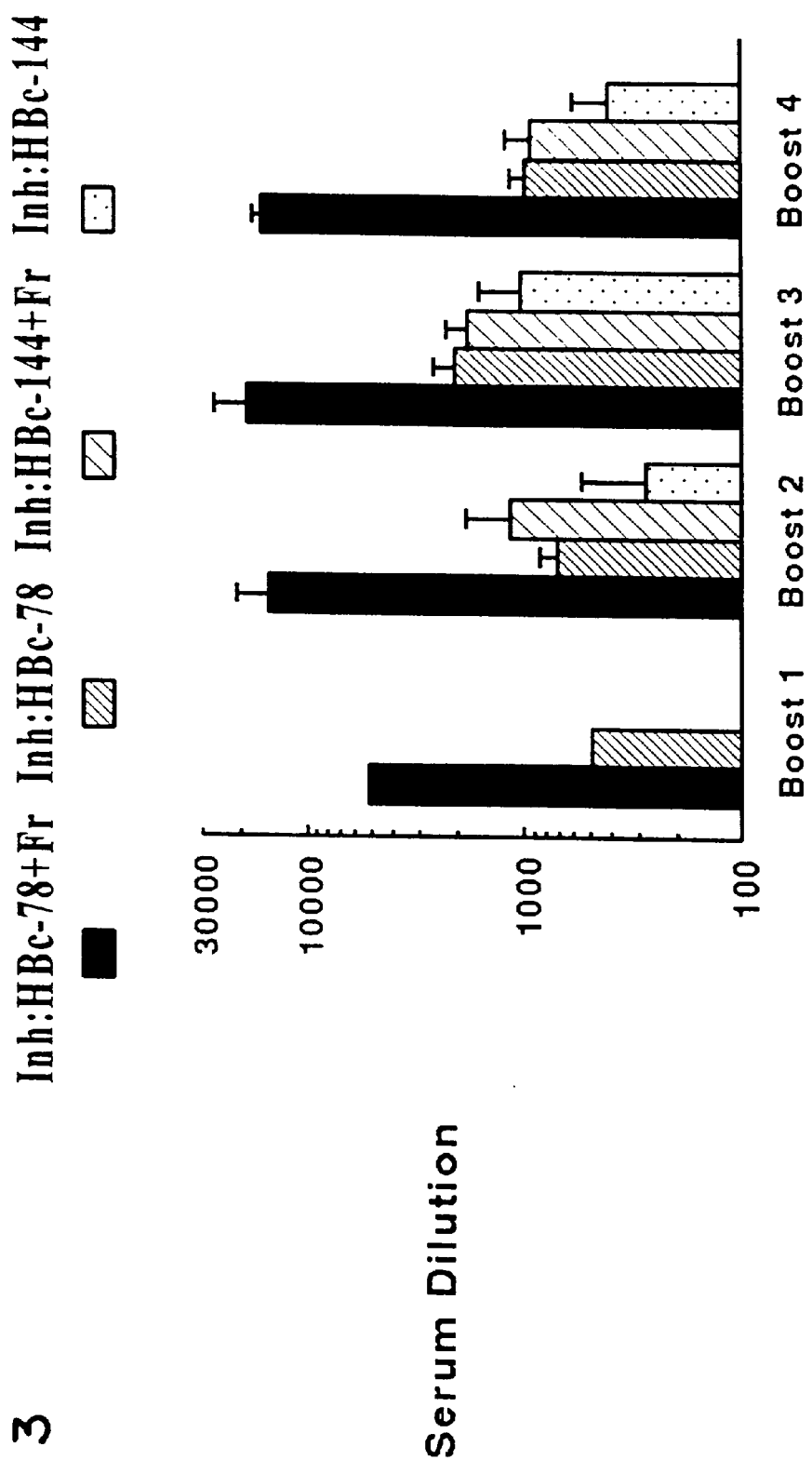
FIG. 3 is a graph showing anti-inhibin antibody titers in mice immunized with Inh:HBc-78 with Fruend's; Inh:HBc, Inh:HBc-78 without Fruend's; Inh:HBc-144 with Fruend's; and Inh:HBc-144 without Fruend's.

The $A_{490}$ for blood samples of HBc-treated mice were not different than the untreated control samples (data not shown). As shown in FIG. 3, significant antibody titers against the $\alpha_c^{1-26}$ inhibin fragment were elicited in all mice immunized with either Inh:HBc-144, Inh:HBc-78, with Fruend's adjuvant (+FR), and importantly, in the absence of the adjuvant. Mice immunized with Inh:HBc-78 plus Fruend's adjuvant demonstrated the highest titer. The values shown in the figure represent the mean ±SEM of pooled mouse titers for Boost 1, but individual mouse titers for Boosts 2–4 are shown.

Figure 4:
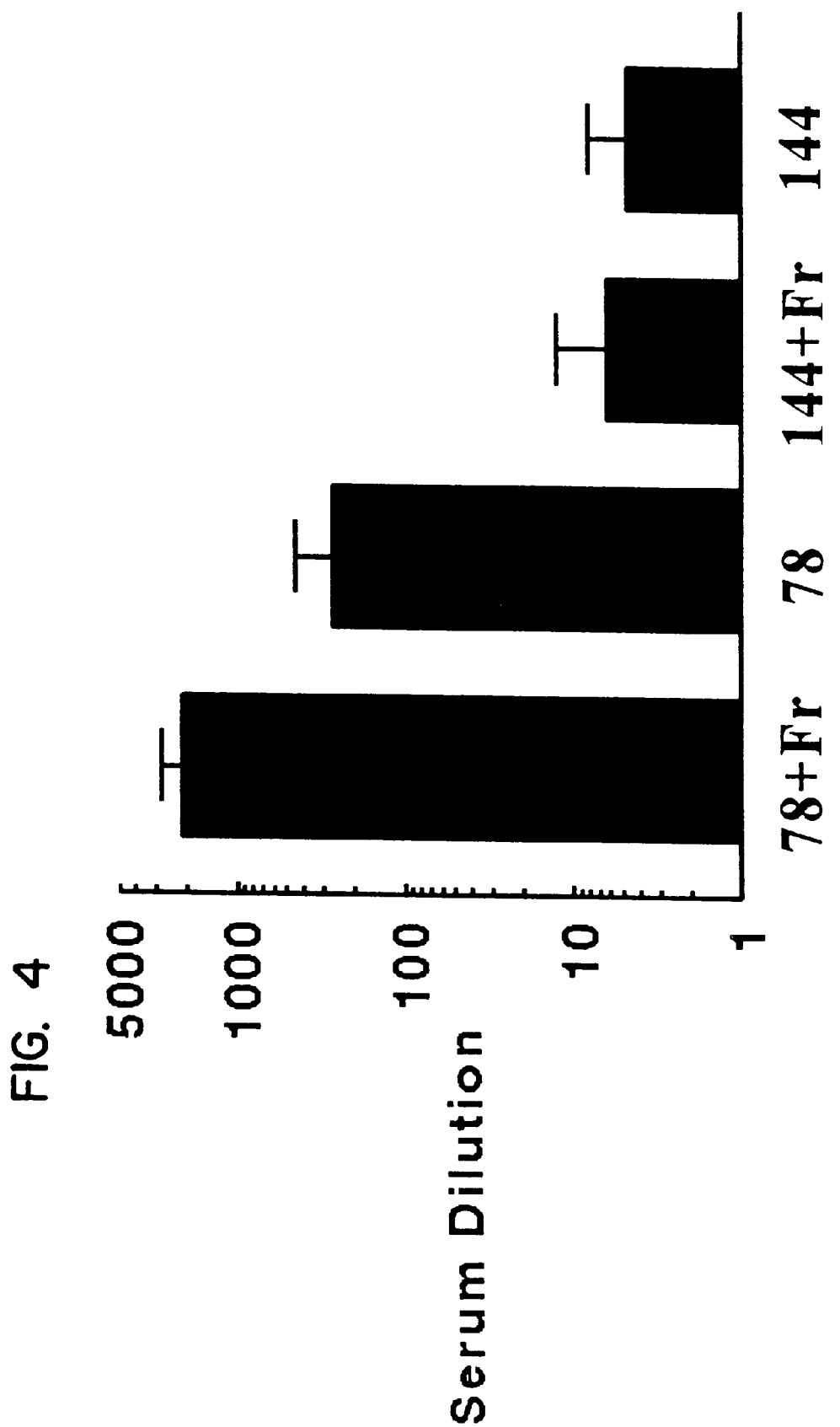
FIG. 4 is a graph showing anti-native inhibin antibody titers in mice immunized with Inh:HBc-78 and Inh:HBc-144 with and without Fruend's.

The immunogenic blood samples were further tested for their ability to recognize native inhibin. Microtiter test plates were coated with 1 μg of a partially purified preparation of bovine inhibin, prepared as described in Good, et al., *Biology Reprod* 53:1478–1488, 1995. The native inhibin preparation contains nine different molecular variants of bovine inhibin dimers and α subunits. Titer was determined for mouse serum collected after Boost 4. The $A_{490}$ values for HBc-treated mice did not differ from the untreated control (data not shown). FIG. 4 shows $A_{490}$ values as mean ±SEM of individual mouse titers for each treatment group after Boost 4. The results demonstrate that mice immunized with any of the HBc- Inhibin fusion proteins, with or without adjuvant, produced antibodies capable of reacting with native inhibin. The Inh:HBc-78 (In4-56) fusion protein produced the highest antibody titers, with or without added adjuvant.

Example 3

Intraperitoneal Immunization of Mice with Inh:HBc

Mice (5 per treatment group) were immunized intraperitoneally with the Inh:HBc fusion proteins Inh:HBc-144 and Inh:HBc-78 or with HBc mixed in Fruend's adjuvant. A boost was given 24 days after primary injection, and titer was determined 7 days after the boost, using the methods described above for Example 2.

In the analysis of antibody titer, serum was pooled for all mice in a treatment group, and 2 μg of the inhibin antigen $\alpha_c^{1-26}$ was added to each well of Maxisorp, NUNC plates. Both controls and treated animals exhibited high titers against HBc (data not shown). Importantly, antibodies against the inhibin antigen were detected for all mice immunized with Inh:HBc-144 or Inh:HBc-78, but not the HBc control (see Table 1). The titers of anti-inhibin antibodies elicited by Inh:HBc-78 were 5 times the level elicited by Inh:HBc-144, and with greater specificity for the inhibin antigen versus the carrier HBc molecule.

TABLE 1

| Immunogen | Anti-HBc Titer | Anit-Inhibin Titer |
|---|---|---|
| Inh:HBc-144 | 1:10,000 | 1:3,000 |
| Inh:HBc-78 | 1:500 | 1:15,000 |
| HBc | 1:100,000 | — |

Example 4

Immunization of Gilts with HBcAg:$\alpha_c^{1-25}$ Fusion Protein

Latvian White gilts, 2 gilts per treatment group, were administered a single dose of 1 mg (0.8 ml) of Inh:HBc fusion protein, Inh:HBc-144 or Inh:HBc-78, or with HBc control, mixed in 0.8 ml Fruend's Complete Adjuvant. Injections were made into multiple sites across each animal's back. Blood samples were collected and titers against the antigenic inhibin 1–26 peptide were determined, as described above for Example 2, assaying individual animal titers.

Figure 5:
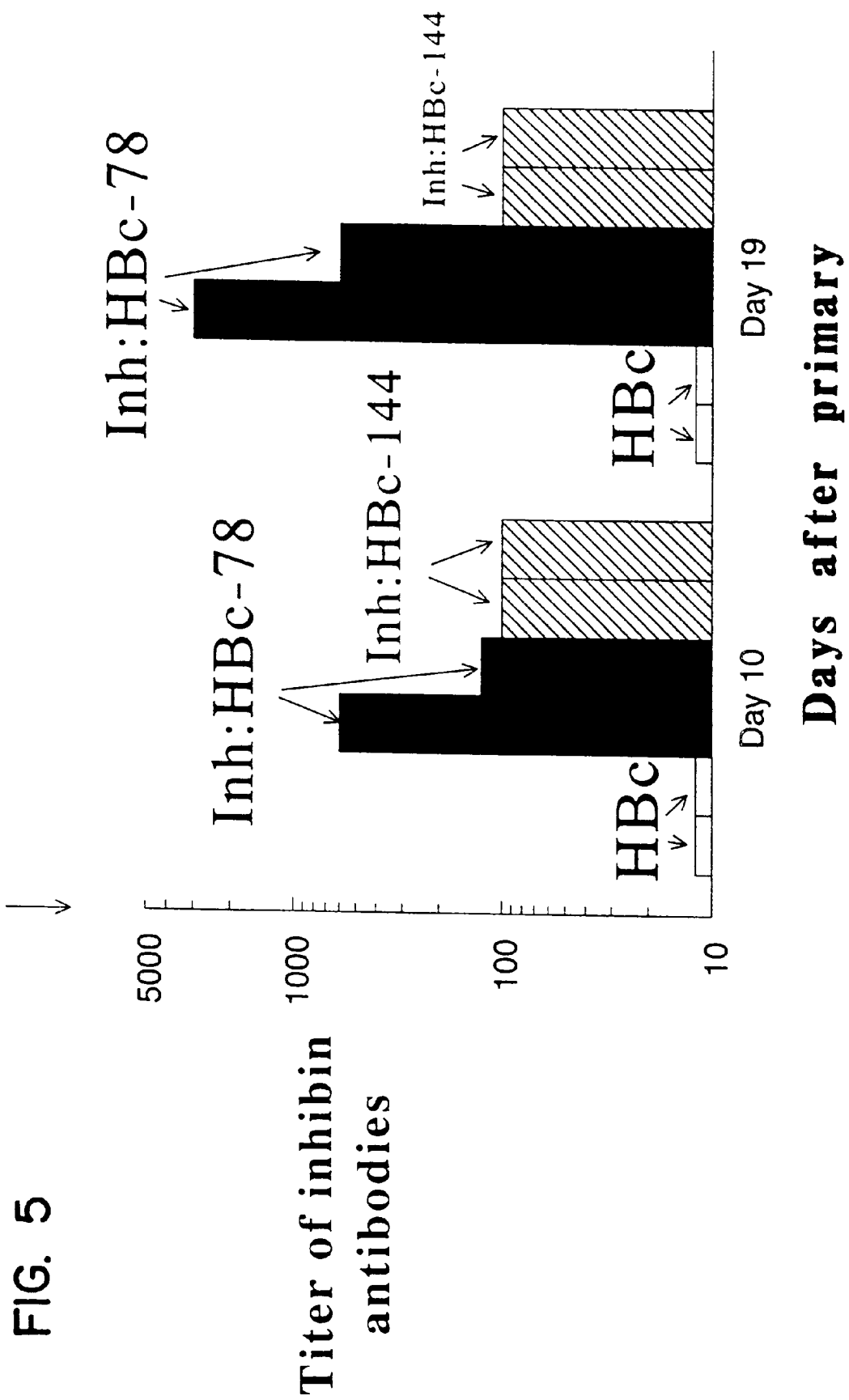
FIG. 5 is a graph showing anti-inhibin titers in gilts immunized with Inh:HBc-144 and Inh:HBc-78.

Within ten days after the single injection, the two gilts immunized with Inh:HBc-78 had developed anti-inhibin titers of 1:600 and 1:125, which increased to 1:3000 and 1:600, respectively, by 19 days after the injection, as shown in FIG. 5. The two gilts immunized with Inh:HBc-144 had titers of 1:125 or less, and the two gilts immunized with HBcAg had non-detectable titers. Thirty days after the primary immunization, the titer determined for each gilt was determined. The 30 day data are shown below in Table 2.

TABLE 2

| Immunogen | anti-HBc | | anti-inhibin | |
|---|---|---|---|---|
| Inh:HBc-78 | 1:10,000 | 1:10,000 | 1:15,000 | 1:3,000 |
| Inh:HBc-144 | 1:100,000 | 1:1,000,000 | 1:100 | 1:125 |
| HBc | 1:100,000 | 1:100,000 | — | |

These results demonstrate that an HBcAg:$\alpha_c^{1-25}$ fusion protein, Inh:HBc-78, is highly immunogenic in gilts, as well as in mice, and the immunogenicity is demonstrated in the absence of adjuvant. The data further demonstrate that an inhibin antigenic peptide, when inserted at position 78 of HBc, induces a useful antibody titer with preferred anti-inhibin specificity.

We claim:

1. A nucleic acid construct comprising:

a first nucleic acid sequence encoding an inhibin antigenic peptide; and a second nucleic acid sequence encoding a hepatitis B capsid protein, wherein the first sequence is inserted into the second sequence to encode a fusion protein having the inhibin antigenic peptide inserted at position 78 of the hepatitis B capsid protein.

2. The nucleic acid construct of claim 1, wherein said second nucleic acid sequence encoding hepatitis B capsid protein is truncated to remove nucleic acid residues 145–183.

3. The nucleic acid construct of claim 1, wherein the inhibin antigenic peptide comprises an antigenic portion of the $\alpha_c$ chain.

4. The nucleic acid construct of claim 1, wherein the inhibin antigenic peptide comprises a sequence of 10 or more of amino acids 1–30 of inhibin $\alpha_c$.

5. The nucleic acid construct of claim 1, wherein the inhibin antigenic peptide comprises inhibin-$\alpha_c^{125}$.

6. A fusion protein comprising:

hepatitis B capsid protein; and an inhibin antigenic peptide, wherein the inhibin antigenic peptide is inserted at amino acid 78 of the hepatitis B capsid protein.

7. The fusion protein of claim 6, wherein the inhibin antigenic peptide comprises an antigenic portion of the $\alpha_c$ chain.

8. The fusion protein of claim 6, wherein the inhibin antigenic peptide comprises a sequence of 10 or more of amino acids 1–30 of inhibin $\alpha_c$.

9. The fusion protein of claim 6, wherein the inhibin antigenic peptide comprises inhibin-$\alpha_c^{1-25}$.

10. A method for producing an anti-inhibin immunogen, the method comprising the steps of:

inserting a first nucleic acid sequence encoding an inhibin antigenic peptide into a second nucleic acid sequence encoding hepatitis B capsid protein to form a fusion construct expressing a fusion protein having the inhibin antigenic peptide inserted at position 78 of the hepatitis B capsid protein;

expressing the fusion protein in a host cell.

11. The method of claim 10, wherein the inhibin antigenic peptide comprises an antigenic portion of the inhibin $\alpha_c$ chain.

12. The method of claim 10, wherein the inhibin antigenic peptide comprises a sequence of 10 or more of amino acids 1–30 of inhibin $\alpha_c$.

13. The method of claim 10, wherein the inhibin antigenic peptide comprises inhibin-$\alpha_c^{1-25}$.

14. A method of inducing an anti-inhibin immune response in a host animal comprising the steps of:

administering to a host animal a fusion protein comprising a hepatitis B capsid protein having an inhibin antigenic peptide inserted at position 78.

15. The method of claim 14, wherein the inhibin antigenic peptide comprises an antigenic portion of the $\alpha_c$ chain.

16. The method of claim 14, wherein the inhibin antigenic peptide comprises a sequence of 10 or more of amino acids 1–30 of inhibin $\alpha_c$.

17. The method of claim 14, wherein the inhibin antigenic peptide comprises bovine inhibin-$\alpha_c^{1-25}$.

18. The method of claim 14, wherein said host animal is swine.

19. The method of claim 14, wherein said administering is in the absence of adjuvant.

* * * * *